United States Patent
Kouznetsov et al.

(10) Patent No.: US 6,250,140 B1
(45) Date of Patent: Jun. 26, 2001

(54) METHOD FOR MEASURING THE RATE OF A FOULING REACTION INDUCED BY HEAT TRANSFER USING A PIEZOELECTRIC MICROBALANCE

(75) Inventors: Dmitri Kouznetsov, Naperville, IL (US); Louis DiSanto, Mishawaka, IN (US); Donald Johnson; Paul R. Kraus, both of Batavia, IL (US); Barbara E. Moriarty, Palatine, IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/338,669

(22) Filed: Jun. 22, 1999

(51) Int. Cl.[7] ............... G01N 17/02; G01N 17/00; G01N 33/00; G01L 3/26; G01H 1/00
(52) U.S. Cl. .................. 73/86; 436/6; 73/61.62; 73/579; 73/116
(58) Field of Search .................................. 73/86

(56) References Cited

U.S. PATENT DOCUMENTS

| Re. 33,468 | 12/1990 | Brindak . |
| 3,913,378 | 10/1975 | Hausler . |
| 4,097,341 | 6/1978 | Schell et al. . |

(List continued on next page.)

FOREIGN PATENT DOCUMENTS

| 1301477 | 5/1992 | (CA) . |
| 676637 A1 | 11/1995 | (EP) . |

OTHER PUBLICATIONS

Paul Kraus, et al., "A Novel Sensor For Monitoring Oilfield Fouling In Near–Real Time", presented at IEE symposium for On–line Monitoring Techniques for the off–shore Industry at Aberdeen Scotland on Jun. 2, 1999.

Shiojiri, Makoto et al. "Thermal Effect of Ultrasonic Vibration of Quartz Crystal Microbalance on Chemical Reactions". *Japanese Journal of Applied Physics*. vol. 10, No. 1. Jan. 1971, pp. 143–148.

Gabrielli, C., et al. "Quartz Crystal Microbalance Investigation of Electrochemical Calcium Carbonate Scaling". *J. Electrochem. Soc.* vol. 145, No. 7. Jul. 1998, pp. 2386–2396.

(List continued on next page.)

*Primary Examiner*—Hezron Williams
*Assistant Examiner*—Katina Wilson
(74) *Attorney, Agent, or Firm*—Margaret M. Brumm; Thomas M. Breininger (57) ABSTRACT

A method measuring a rate of fouling caused by a heat flux through the surface subjected to electrochemical polarization. The method includes the steps of: providing a piezoelectric microbalance comprising a piezoelectric material with electrodes disposed thereon; exposing the working electrode of the microbalance to a flowing liquid, the liquid containing at least one fouling forming species; maintaining the liquid at a constant first temperature; maintaining the liquid at required hydrodynamic conditions; applying either a constant heat flux through the microbalance resulting in its working electrode having a variable second temperature or applying a variable heat flux through the microbalance resulting in its working electrode having a constant second temperature; and measuring a rate of fouling on the microbalance surface. The method also comprises measuring the surface density and heat transfer resistance of the deposit independently, thereby the corresponding ratio can be determined contributing to the deposit identification. The working electrode of the microbalance can be subjected to an electrochemical polarization in a wide range to systematically simulate the conditions of heat exchange surface produced by corrosion or other electrochemical processes. The possibility to apply electrochemical polarization, cooling or heating flux in the direction opposite to that causing fouling can be used to clean the immersed microbalance surface in-situ.

29 Claims, 3 Drawing Sheets

U.S. PATENT DOCUMENTS

| | | | |
|---|---|---|---|
| 4,539,846 | * | 9/1985 | Grossman .............................. 73/579 |
| 4,561,286 | | 12/1985 | Sekler et al. . |
| 4,808,538 | * | 2/1989 | Roffey et al. ........................... 436/6 |
| 5,162,077 | | 11/1992 | Bryan et al. . |
| 5,201,215 | | 4/1993 | Granstaff et al. . |
| 5,208,162 | * | 5/1993 | Osborne et al. ........................ 436/6 |
| 5,479,818 | * | 1/1996 | Walter et al. .......................... 73/116 |
| 5,484,626 | | 1/1996 | Storjohann et al. . |
| 5,487,981 | | 1/1996 | Nivens et al. . |
| 5,661,233 | | 8/1997 | Spates et al. . |
| 5,734,098 | | 3/1998 | Kraus et al. . |
| 5,827,952 | | 10/1998 | Mansure et al. . |
| 6,053,032 | * | 4/2000 | Kraus et al. ........................ 73/61.62 |

OTHER PUBLICATIONS

Klavetter, E.A., et al. "Monitoring Jet Fuel Thermal Stability Using a Quartz Crystal Microbalance". *Energy and Fuels* 1993, 7, 582–588.

Kouznetsov, D., et al. "Investigation of Electrosorption of a Quarternary Ammonium Salt Using an Electrochemical Quartz Crystal Microbalance". *Electrochimica Acta*. vol. 40, No. 10, pp. 1513–1521, 1995.

"DATS Fouling Monitor System". Bridger Scientific, 1992, (1–106).

Kuzay, Tuncer M., et al. "A Special Heat Transfer Monitor (HTM) For the Trane Company OTEC Heat Exchanger". Argonne National Laboratory. Feb. 1981. (1–69).

Knudsen, James G. "Apparatus and Techniques for Measurement of Fouling of Heat Transfer Surfaces". As published in Somerscales, E.F.C., et al. *Fouling of Heat Transfer Equipment*. Hemisphere Publishing. 1981. Mar. 1979. (57–81).

Piron, D.L. "The Electrochemistry of Corrosion". NACE.

Smyk, E.B., et al. "The Design and Application of Polymers in Cooling Water Programs". National Association of Corrosion Engineers. Mar. 1988. (1–10).

1998 Standard for "Water Chilling Packages Using the Vapor Compression Cycle", American Refrigeration Institute. Standard 550/590.

Nace International. "Standard Recommended Practice On–Line Monitoring of Cooling Waters". NACE Standard RPO189–95 Item No. 21041, 1995, (1–14).

Jope, Dirk, et al. "Application of a Quartz Crystal Microbalance to the Study of Corrosion Inhibitors". The Electrochemical Society Proceedings. vol. 94–26. (161–166).

Bott, T.R. "Fouling of Heat Exchangers". 1995, (479–516).

Rosset, Robert, et al. "Determination of the Anti–Scale Effect of Acid Vaccination by Chronoamperometry and Chronoelectrogravimetry". *Electrochemistry*. 1993. (1711–1715). (English Language Abstract).

Zidoune, Moussa, et al. "Demonstration of the Anti–Scale Effect of Aminotris–(methylenephosphonic) Acid by Chronoamperometry and Chronoelectrogravimetry". *Electrochemistry*. 1992. (795–799) (English Language Abstract).

Khalil, Abdelali, et al. "Water Scaling Tendency Characterization by Coupling Constant Potential Chronoamperometry With Quartz Crystal Microbalance". *Electrochemistry* 1992. (145–149). (English Language Abstract).

Bott, T.R. "Fouling Notebook". 1990, (118–123).

\* cited by examiner

METHOD FOR MEASURING THE RATE OF A FOULING REACTION INDUCED BY HEAT TRANSFER USING A PIEZOELECTRIC MICROBALANCE

FIELD OF THE INVENTION

The present invention relates generally to a method for rating the fouling propensity of industrial fluids, rating the effectiveness of anti-fouling treatments, and for the application of process controls to minimize fouling. More specifically, the present invention relates to a method of assessing the mass rate of deposition resulting from a chemical reaction in a process fluid caused by a heat flux through the immersed equipment surfaces also subjected to an electrochemical polarization.

BACKGROUND OF THE INVENTION

The operating efficiency of industrial and domestic systems largely depends on cleanliness of their surfaces exposed to process fluids and subjected to natural or induced heat transfer and electrochemical conditions. Untreated process fluids contain a number of constituents the solubility of which can substantially decrease in certain temperature and pH ranges resulting in scaling or precipitation on the surface of an apparatus or a vessel. These processes, otherwise known as fouling, impede the proper flow of heat through the equipment surfaces, which leads to an overall decrease of the system operating efficiency.

Further, in a system where the fluid or liquid is flowing or being pumped, the formation of scales and deposits decreases the diameter of passages, increases the flow resistance and mechanical stresses thereby increasing the risk of structural damage as well as energy costs. Also, the formation of scales and deposits on metal surface favors localized and under deposit corrosion, thereby reducing the operating lifetime of the equipment.

Fouling can be a function of many factors: liquid temperature and chemistry; physical characteristics of the flow such as Reynolds number, shear stress and viscosity; geometry of the equipment; materials of construction; and temperature of the heat transfer surface. The most important liquid characteristics are the level of dissolved solids, the presence of microbiological matter and the process chemistry. Liquid velocity, shear stress and viscosity are the determinant flow characteristics.

Induced fouling deposits can form on surfaces that are either colder or warmer than the temperature of the bulk liquid. For example, in industrial processes employing water-cooled heat exchangers, silicate scale deposits can form on surfaces that are colder than the bulk water while carbonate and sulfate deposits can form on surfaces warmer than the bulk water. Another example of fouling of a colder surface is the formation of ice from water or the solidification of wax laden hydrocarbons while transporting fluids containing these substances in pipelines exposed to low temperatures.

Further, an electrochemical polarization in the form of potential or current naturally or intentionally applied to a heat transfer surface may significantly affect fouling due to the electrochemical reactions induced at the equipment surface. For example, the surface pH increase induced electrochemically by corrosion results in the increase of the deposition rate of calcium carbonate scale on a mild steel heat exchange surface compared to that made of stainless steel. Corrosion results in the formation of anodic and cathodic sites on mild steel surface immersed in water at ambient conditions. Reduction at the cathodic sites of the oxygen dissolved in water leads to a near surface pH increase that favors precipitation of carbonate scales. In another example mild steel industrial heat exchangers are often protected against corrosion using cathodic polarization using sacrificial anodes or imposed current. A commonly accepted cathodic protection criterion for mild steel parts is the application of a negative potential which results in the increase of the near surface pH which favors carbonate scaling. The use of two or more different metals in constructing a heat exchanger can subject one of them to a positive potential sufficiently high to result in water oxidation which produces a near-surface excess of $H^+$ ions, and thus, a pH decrease will occur resulting in the scale dissolution.

The decrease of the heat exchange at a surface due to fouling is defined by the fouling thermal resistance, $R_f$ as:

$$R_f = 1/U_{fouled} - 1/U_{clean} \tag{1}$$

where $1/U_{clean}$ and $1/U_{fouled}$ are the heat transfer coefficients of the surface in clean and fouled conditions, respectively. The heat transfer coefficients are defined as:

$$T_{wall\ clean} - T_{bulk} = 1/U_{clean}(Q/A) \tag{2a}$$

$$T_{wall\ fouled} - T_{bulk} = 1/U_{fouled}(Q/A) \tag{2b}$$

where $T_{wall\ clean}$ and $T_{wall\ fouled}$ are the temperatures of the surface in clean and fouled conditions, respectively; $T_{bulk}$ is the bulk temperature of the process fluid; Q/A is the heat flux through the heat exchange surface having area A.

Thus, the fouling resistance may be determined by measuring the change of heat transfer through a given surface over time.

As shown in Equations 2a and 2b above, the measurement of fouling resistance requires the knowledge of the heat transfer resistance of the same surface at clean conditions. This brings unavoidable uncertainty because the heat transfer resistance of a clean surface depends on the thermal resistance of the clean surface itself, $R_{wall}$, and the thermal resistance of the process fluid, $R_{fluid}$:

$$1/U_{clean} = R_{wall} + R_{fluid} \tag{3a}$$

combining equations (1) and (3a):

$$1/U_{fouled} = R_f + R_{wall} + R_{fluid} \tag{3b}$$

The thermal resistance of the fluid is highly dependent upon the fluid flow rate as shown in Equation 4 below:

$$1/U_{clean} = R_{wall} + C/V^n \tag{4}$$

where C is the constant, V is the velocity of the fluid and $R_{wall}$, C and n can be obtained through calibration of the heater.

Measurements as described above may result in artificially low or even negative values of thermal resistance during the initial operating period. This happens due to the initial deposits increasing the roughness of the heat exchange surface which consequently decreases surface-to-fluid thermal resistance. As a result, the actual increase in thermal fouling resistance may not be detected. As reported by J. Knudsen, "Apparatus and Technologies for Measurement of Fouling of Heat Transfer Surfaces, and Fouling of Heat Transfer Equipment", Proceedings of an International Conference, Rensselaer Polytechnic Institute, pp. 57–82 (1979), as the fouling layer thickens, the effect of the lower thermal conductivity dominates the improved local heat transfer coefficient due to roughening and the fouling resistance again becomes positive. Therefore, the common heat transfer resistance measurements have a minimal fouling limit below which they cannot reliably detect or determine $R_f$. This presents a substantial obstacle especially when effective anti-fouling treatments are being screened or tested.

Although important from the technical standpoint, the measurement of fouling thermal resistance does not provide a strict quantitative answer as to how a certain treatment affects the deposition mass rate of the fouling deposit. This deposition mass rate represents the velocity of mass accumulation of fouling deposit per square unit of area per unit of time and is expressed as follows:

$$m_f = R_f(\rho_f k_f) \quad (5)$$

wherein $m_f$ is the deposit mass per unit area per unit of time; $R_f$ is the thermal fouling resistance; $\rho_f$ is the density of the fouling deposit; and $k_f$ is the thermal conductivity of the fouling deposit.

Traditionally, coupons or forensic investigation were used to determine $m_f$, the mass of deposit on the scaled surface. However, the employment of a piezoelectric microbalance makes this task relatively easy to accomplish in real time and in situ. The principle of piezoelectric mass measurement is based upon the property of a quartz resonator to change its mechanical resonance frequency fo proportionally to the mass and viscoelastic properties of the deposited material. U.S. Pat. No. 5,201,215 discloses a method for the simultaneous measurement of the mass loading and fluid property changes using such a quartz crystal microbalance apparatus. The change in frequency is expressed as follows:

$$\Delta f \approx -\frac{2 f_0^2}{N(\mu_\mu, \rho_q)1/2}\left[\rho_s + \left(\frac{\rho\eta}{4\pi f_0}\right)^{1/2}\right] \quad (6)$$

where $f_0$ is the unperturbed resonant frequency of the quartz crystal; N is the harmonic number; $\mu_\mu$ is the quartz shear stiffness, $\rho_q$ is the density of quartz; $\rho_s$ is the surface mass density of the deposit (mass/area), $\rho$ is the density of the medium contacting the resonator and $\eta$ is the viscosity of the medium contacting the resonator.

Those skilled in the art use electronic circuit analysis methods to determine the separate contributions from the mass and viscoelasticity of the deposit. Also known are equations used for thick deposits when the change of resonant frequency is higher than 10%. However, in the case of a crystalline non-viscous deposit when the change is less than 10% (which corresponds to approx. 8900 $\mu g/cm^2$, or 32 micron layer of calcium carbonate with the density of 2.76 g/cm3) a simplified expression can be used:

$$\rho_s = -C \Delta f_0 \quad (7)$$

where C is determined by calibration and is typically equal to $1.77 \times 10^{-2}$ $\mu g/(sec\ cm^2\ Hz)$ for a 5 MHz quartz crystal.

The use of a piezoelectric microbalance allows the measurement of the effects of electrochemical or chemical reactions on the formation of the scale or deposit on the electrode disposed on the quartz crystal surface. See European Patent Application No. 676 637 A1.

Although useful for comparing the effect of antifouling treatments, electrochemical methods do not simulate a heat exchange surface and form deposits with morphology different than those caused by heat transfer. Electrochemical methods rely upon the precipitation of scale deposits driven solely by the electrolysis of the water solutions and without any contemplation of the chemical effect of the heat transfer. The scale precipitation is driven by the electrochemical reduction of dissolved oxygen and water in the range of −1 V versus saturated calomel electrode (SCE), which results in a pH increase near the electrode. This is limited in that some process streams may not contain dissolved oxygen or water and some forms of fouling may not be driven by a pH increase near the electrode. Further, the accuracy of the electrochemical methods may be affected by the electrochemical reduction of other solution species such as nitrates. The electrochemical methods are based upon the effect of polarization with a definite sign and magnitude. In this way they can not provide data on how scaling is affected by an electrochemical polarization applied beyond the specified limits.

Further, piezoelectric probes become fouled during the tests and typically must be removed from the solution for cleaning. As a result, testing procedures are delayed and are therefore more costly. Surprisingly enough the prior art does not teach us a suitable in-situ method of cleaning.

Therefore, there is a need for a precision method that can measure the mass rate of a fouling reaction that is driven by the supply or withdrawal of heat (to or from the fluid) through the surface subjected to electrochemical polarization. The precision of the method should be as high as it is given by the use of a piezoelectric microbalance. The exploration of the effect of electrochemical polarization should be allowed in the entire cathodic or anodic range so as to simulate the polarization naturally occurring or artificially induced in the industrial equipment. Further, there is a need that the method would allow consecutive measurements without the need to withdraw the probe surface from the liquid being tested or dismantling the testing apparatus, and without the use of additional chemicals. It is also desirable that the probe cleaning could be done electrochemically under the condition that the material of the sensor electrode is not degraded by the cleaning. It is also desirable that the probe cleaning could also be done by communication to the fouling deposit of a certain heat flux in direction opposite to that caused the formation of the deposit.

SUMMARY OF THE INVENTION

A first aspect of the present invention is a method for measuring a rate of scale formation on a surface caused by a flowing liquid and a heat flux through the surface, the method comprising: providing a piezoelectric microbalance comprising piezoelectric material having a first side facing the liquid and a second opposing side, the first side engaging a working electrode, the second side engaging a second electrode; exposing the working electrode of the piezoelectric microbalance to the flowing liquid, the liquid containing at least one fouling species; maintaining the liquid at a constant first temperature; maintaining the liquid in a controlled flow environment; establishing a constant heat flux through the working electrode resulting in the electrode having a variable second temperature; and measuring a rate of precipitation on the electrode.

The second aspect of the instant claimed invention is a method for measuring a rate of scale formation on a surface caused by flowing liquid and a heat flux through the surface, the method comprising: providing a piezoelectric microbalance comprising piezoelectric material having a first side facing the liquid and a second opposing side, the first side engaging a working electrode, the second side engaging a second electrode; exposing the working electrode of the piezoelectric microbalance to a flowing liquid, the liquid containing at least one fouling species; maintaining the liquid at a constant first temperature; maintaining the liquid in a controlled flow environment; applying a variable heat flux across the piezoelectric material to maintain the working electrode at a constant second temperature; and measuring a rate of precipitation on the surface of the piezoelectric material and working electrode.

A third aspect of the instant claimed invention comprises all the actions described above with the addition of applying an electrochemical polarization (potential or current) to the immersed electrode of the microbalance.

A fourth aspect of the instant claimed invention is a method for measuring the effectiveness of an anti-fouling additive in preventing fouling at a solid-liquid interface disposed in a flowing liquid and subjected to a heat flux, the method comprising: providing a piezoelectric microbalance comprising a piezoelectric material having a first side facing the liquid and a second opposing side, the first side engaging a working electrode, the second side engaging a second electrode, the second side of the piezoelectric material engaging a heat conductive material connected to a heat flux generator; exposing the working electrode to the flowing liquid, the liquid containing at least one fouling forming species; maintaining the liquid at a constant first temperature; maintaining the liquid in a controlled flow environment; simultaneously applying a heat flux through the piezoelectric material and the working electrode to maintain the working electrode at a constant second temperature and applying an electrochemical polarization to the working electrode; measuring a rate of precipitation using the piezoelectric material and working electrode; adding the anti-fouling additive to the liquid; and repeating the step of measuring the rate of precipitation using the piezoelectric microbalance.

A fifth aspect of the present invention is a method for measuring the effectiveness of an anti-fouling additive in preventing fouling at a solid-liquid interface disposed in a flowing liquid and subjected to heat transfer, the method comprising: providing a piezoelectric microbalance comprising a piezoelectric material having a first side facing the liquid and a second opposing side, the first side engaging a working electrode, the second side engaging a second electrode, the second side engaging a heat conductive material connected to a heat flux generator; exposing the working electrode to the flowing liquid, the liquid containing at least one fouling species; maintaining the liquid at a constant first temperature; maintaining the liquid in a controlled flow environment; simultaneously applying a constant heat flux through the piezoelectric microbalance to maintain the working electrode thereof at a variable second temperature and applying an electrochemical polarization to the electrode; measuring a rate of precipitation using the piezoelectric microbalance; adding the anti-fouling additive to the liquid; repeating the step of measuring the rate of precipitation using the piezoelectric microbalance.

A sixth aspect of the present invention is that measuring at the solid-liquid interface a mass rate together with heat transfer resistance of fouling reactions allows assessing the product of the density and thermal conductivity of the deposit, which is characteristic of the deposit chemical composition.

A seventh aspect of the present invention is an apparatus for measuring a rate of scale formation on a solid-liquid interface caused by a heat flux through the surface, the apparatus comprising: a piezoelectric microbalance comprising a quartz crystal, the quartz crystal with its surfaces at least partially covered with contact electrodes, whereas a first surface is exposed to the liquid and a second surface is disposed near a heat conducting block, the second surface and block being isolated from the liquid, the heat conducting block being connected to a heat flux generator.

An eighth aspect of the present invention is that the probe cleaning can be done in situ by communication to the fouling deposit of an electrochemical polarization or a certain heat flux with the sign opposite to that which caused the formation of the deposit.

DETAILED DESCRIPTION OF THE PRESENTLY PREFERRED EMBODIMENTS

The present invention provides a method and an apparatus for the measurement of the rate of a chemical reaction induced by the supply or withdrawal of heat through the solid-liquid interface that can be subjected to an electrochemical polarization in a wide range. In this way the present invention simulates those situations where an electrochemical polarization occurs either naturally or artificially at the surface of industrial equipment such as a heat exchanger, cooling tower, boiler, etc. Further, the electrochemical polarization or heat flux can be reversed for purposes of cleaning the sensor.

Precise simulation of heat transfer and polarization allows revealing which of those effects dominates fouling in a real system under given conditions. As a result, the method and apparatus of the present invention more accurately simulate the conditions under which scales are formed on the surface of a piece of industrial equipment.

Figure 1:
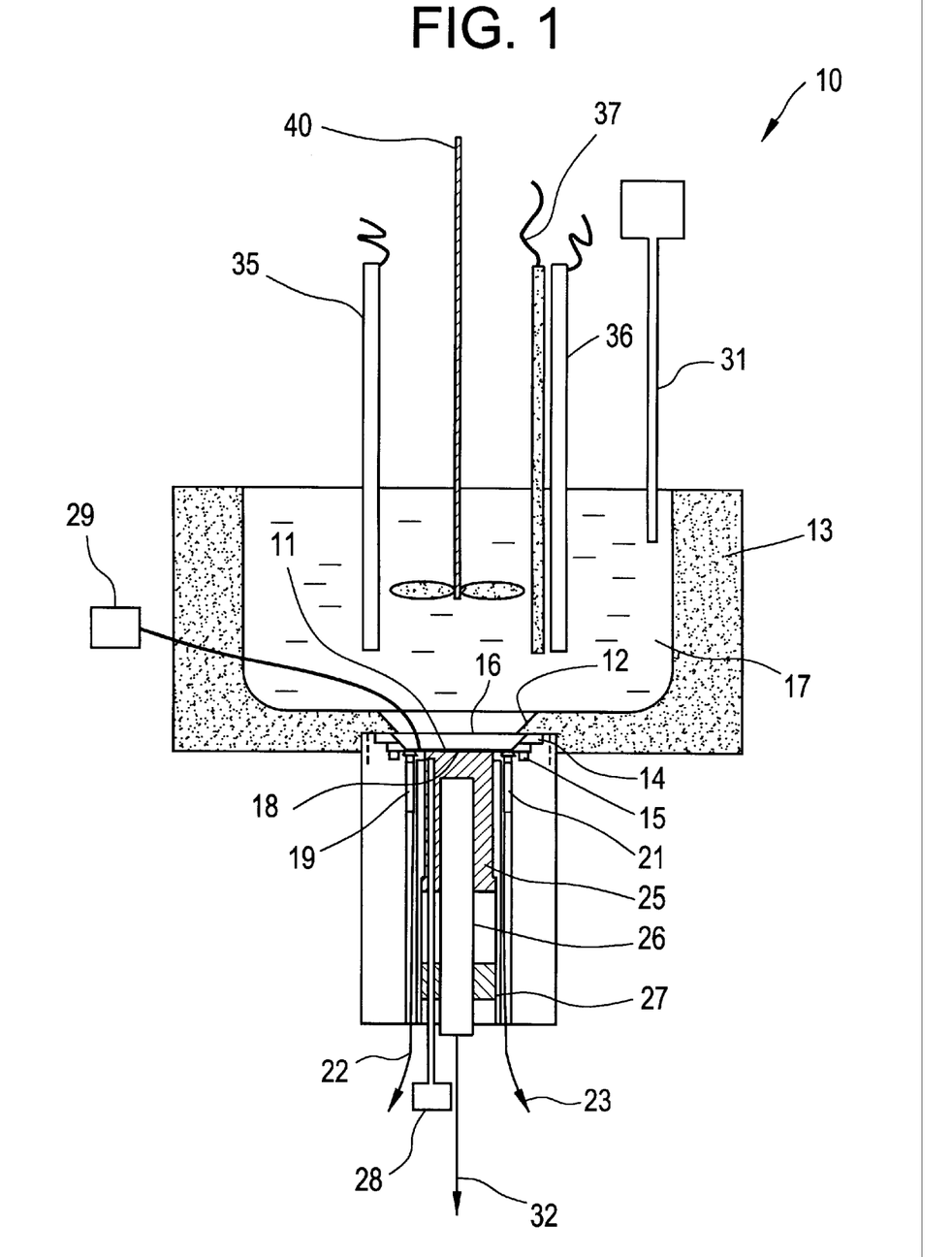
FIG. 1 illustrates, schematically, an apparatus for the simulation of a fouling of an immersed surface induced by heat transfer that includes a piezoelectric microbalance, an electrochemical module and a heat flux generator.

Turning to FIG. 1, an apparatus 10 for carrying out the method of the present invention is illustrated schematically. A quartz crystal 11 is sealed in an aperture 12 of a tank 13. A retainer ring 14 and at least one O-ring 15 insure that only the first side or top side 16 of the quartz crystal is exposed to the test liquid 17 and that the lower side or second side 18 of the crystal 11 is exposed only to air. Spring-loaded contacts are shown at 19, 21 which operatively connect the connecting leads 22, 23 respectively to the crystal electrodes. The leads 22, 23 are then connected to the quartz crystal microbalance monitor 24 (see FIG. 4). A copper block is shown at 25 which accommodates a cartridge heater 26 or a heat flux generator. Suitable heat flux generators include Peltier elements, other forms of heaters or other forms of cooling elements. It will be noted that the apparatus 10 can be employed for a heat flow through the quartz crystal 11 to the test liquid 17 or vice versa. A washer 27 holds the cartridge heater 26 in place. The heater thermocouple is shown at 28; the quartz crystal microbalance skin thermocouple is shown at 29 and the bulk liquid thermocouple is shown at 31. Bulk liquid thermal regulating means can be employed including, but not limited to, a cooler or heater coil disposed in the bulk liquid 17 or tank 13. These and other temperature regulating means will be apparent to those skilled in the art.

The leads 32 connect the heater 26 to a power supply. The electrodes 35 and 36, along with the reference electrode 37 are part of the electrochemical module 38 (see FIG. 4). An impeller 40 provides a steady flow of the bulk liquid 17 past the quartz crystal 11. Impeller 40 could be replaced by any other suitable stirring device, such as a magnetic stirring rod. By "steady ", a relatively constant flow is intended to be provided past the quartz crystal 11. That flow may be either laminar or turbulent; with flow dynamics kept as close as practical to that of the simulated system. The latter is also true for the temperatures which are required for some embodiments of the method of the present invention. The apparatus in FIG. 1 is designed to provide effectively controlled heat transfer through the microbalance working surface (or electrode 42; see FIG. 2) as measured by the thermocouple 29. The temperature of the bulk liquid 17 as measured by the thermocouple 31 can be maintained constant or be varied, as much as is practical to simulate the desired system. The thermocouple 28 is intended to measure the temperature of the cartridge heater 26 or other suitable heat flux generator that should be able to provide the required heat flux through the quartz crystal.

As discussed above, the method of the present invention can be practiced in two principle ways: either a constant heat flux is applied through the quartz crystal 11 which results in a temperature measured by the thermocouple 29 changing along with the crystal fouling or, the heat flux generator 26 can be operated to maintain a constant temperature at the quartz crystal 11 (or electrode 42) thereby providing a heat flux through the quartz crystal changing to overcome the heat transfer resistance of the fouling deposit.

Figure 2:
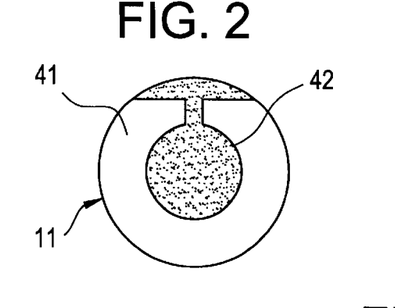
FIG. 2 is a top plan view of the quartz sensor of the piezoelectric microbalance device shown in FIG. 1.
Figure 3:
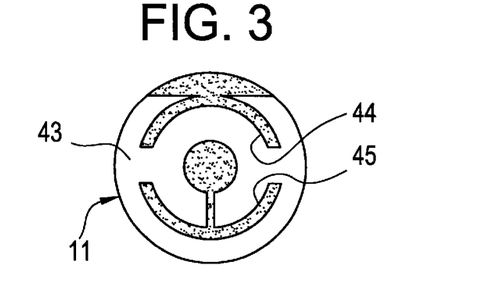
FIG. 3 is a bottom plan view of the quartz sensor of the piezoelectric microbalance device shown in FIG. 1.

In a preferred embodiment, the mass sensing element of the piezoelectric microbalance represents an AT cut quartz crystal 11 with evaporated electrodes 42 and 43 shown in FIG. 2. The electrodes may be produced by vacuum sputtering titanium with or without additional sputtering an upper layer of gold. Electrode 42 is considered working as it is immersed into the tested fluid during measurements. The specific material used for the upper layer of the electrode 42 will depend upon the particular type of fouling surface to be investigated. In any case it is preferable that the materials of electrode 42 do not degrade during electrochemical cleaning. Those skilled in the art can use a variety of film deposition technologies to prepare the electrodes. For example, the outer electrode coating can be made by evaporation, or plating any metal or drying the solution of a non-metal material to investigate its affinity to a particular type of fouling. Electrode 42 wraps around the edge of the crystal to its bottom side 43 to form contact 44 as shown in FIG. 3. The bottom side 43 of the quartz crystal 11 includes also a second excitation electrode with contact 45. The contacts 44 and 45 provide electrical connections with the quartz sensor monitor 24 (see FIG. 4) by way of the connecting wires 22, 23 (see FIG. 1).

Returning to FIG. 1, the metal block 25 is preferably made of copper due to its good heat conductivity and is preferably disposed slightly below the lower or air side 43 of the crystal 11. The metal block is manufactured to accommodate a heating of cooling element such as the cartridge heater 26 illustrated or a Peltier element, an air cooler, or refrigerating rod.

The heat flux entering or exiting the bulk liquid is measured by the thermocouples 29 and 31. The thermocouple 29 preferably has a narrow diameter of about 0.25 mm or less. Also, instead of the thermocouple 29, the temperature of the microbalance surface can be measured using a thermocouple junction or thermistor evaporated on either surface 41 or 43 of the quartz crystal 11. Again, as noted above, either a constant heat flux may be applied through air, or any convective or conductive medium, in a fashion perpendicular to the crystal 11 or a constant skin temperature can be maintained, by using a heating element in direct contact with the surface of crystal 11. In either case, the crystal 11 acquires a temperature higher or lower than the bulk fluid 17, depending upon the type of simulation required.

Figure 4:
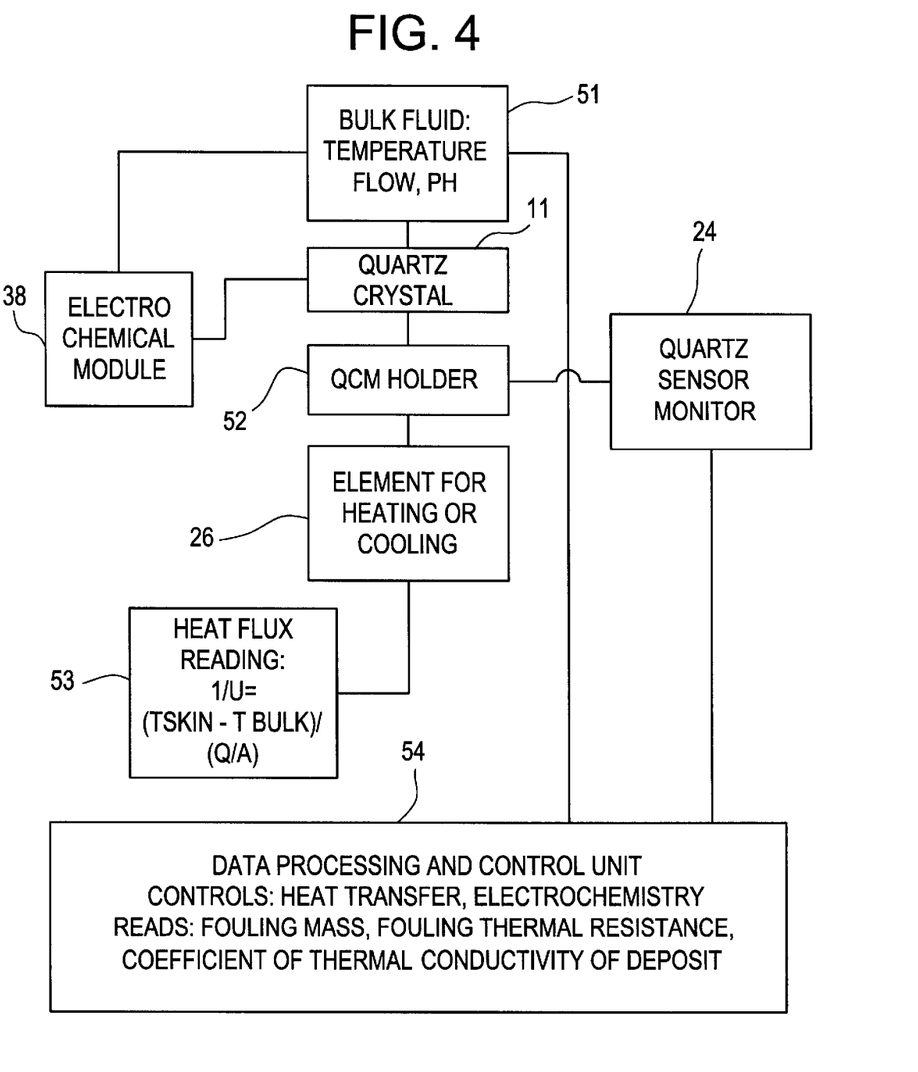
FIG. 4 is a block diagram of one embodiment of the present invention.

Referring to FIGS. 4 and 1, the electrochemical module 38 comprises graphite counter electrodes 35, 36 electrolytically connected to the bulk fluid 17 and capable of applying a uniform electric field to the fluid side electrode 42 (see FIG. 2) of the piezoelectric microbalance. The counter electrodes 35, 36 may also be manufactured from other resistant materials such as platinum, or stainless steel. Other materials will be apparent to those skilled in the art. A preferred embodiment uses a three electrode potentiostatic arrangement with a saturated calomel reference electrode 37 located in the fluid 17 at a distance of about 1 cm in front of the microbalance electrode 42. However, a reference electrode 37 may not be necessary for a galvanostatic operation. In principle, any electric source capable of supplying to the working electrode the current or potential of suitable magnitude, polarity and stability can be used. The electrical conditions establishing in the circuits can be controlled and measured using the equipment commonly used by those skilled in the art. The electrodes 35, 36 and 37 are employed either to simulate a naturally occurring electrochemical polarization, to provide an artificial electrochemical polarization, or provide the polarization necessary to clean the working electrode 42 disposed on the quartz crystal 11.

Turning to FIG. 4, the module 51 is connected to the thermocouple 31 for measuring the temperature of the bulk fluid 17. Also, pH, flow rate, and other sensors may be incorporated to follow the chemical and flow parameters of the liquid, which are not illustrated in FIG. 1. The quartz crystal microbalance holder 52 refers to the assembly holding and sealing the crystal 11 including spring loaded contacts 19, 21 and electrical leads 22, 23. The module 53 refers to the thermocouples 29, 31. The calculations and control of test parameters are performed by a unit shown at 54.

Figure 5:
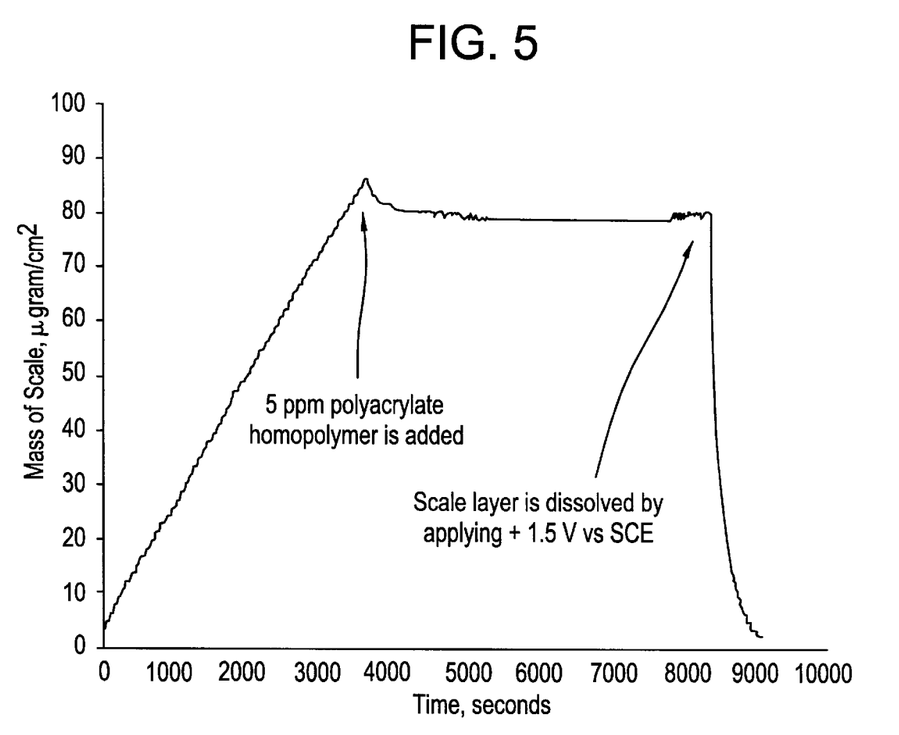
FIG. 5 illustrates, graphically, the ability of an embodiment of the present invention to monitor the effectiveness of an anti-fouling treatment. Specifically, a solution of 300 ppm of $CaCl_2 \times 2H_2O$ and 300 ppm of $NaHCO_3$ both as $CaCO_3$ at 30° C. served as the bulk liquid. No electrochemical polarization was applied. The apparatus of the present invention was operated in a mode of constant skin temperature of 30.5° C. Polyacrylate homopolymer in concentration of 5 ppm was added to the solution after 3200 seconds. After 8500 seconds the microbalance electrode was cleaned from fouling deposit by applying an anodic potential of +1.5 V versus saturated calomel electrode.

An example is illustrated in FIG. 5. A model cooling water solution containing 300 ppm of $CaCl_2 \times 2H_2O$ and 300 ppm of $NaHCO_3$ both as $CaCO_3$ was held at a constant temperature of 30° C. A 40-watt cartridge heater 26 was installed inside the copper block 25 in the holder of quartz crystal microbalance. The microbalance uses a 5 MHz overtone polished AT-cut quartz crystal with evaporated gold over titanium electrodes. The fluid side electrode 42 had a diameter of 12.5 mm (0.5"). The heat conducting block 25 had the diameter of the fluid side electrode 42 and was located 0.2 mm below the surface of the quartz sensor 11 from the air side and was thermally insulated from the outside environment. The device was operated in a constant skin temperature mode so that the heat flux supplied by the heater 26 was adjusted to provide a constant skin temperature of 30.5° C. measured by an ungrounded thermocouple 29 of 0.25 mm in diameter attached to the fluid side of the microbalance near the electrode 42. A steady flow of solution 17 was maintained over the entire sensor surface. As shown in FIG. 5, precipitation of carbonate scale starts almost immediately at a constant rate as the heat flux establishes through the crystal surface. After approximately one hour, when a scale layer of 85 $\mu g/cm^2$ was accumulated, 5 ppm of polyacrylate homopolymer was added, which stopped further scale deposition within seconds. The experiment was continued for the next 1.4 hours while the deposition rate was less than 2 $\mu g/cm^2$/hour. In the end of the experiment, the microbalance surface was cleaned from deposit by applying a positive potential of +1.5V vs. saturated calomel electrode 37 to the working electrode 42 using the counter electrodes 35, 36.

In another example, the apparatus 10 can be used for evaluating and screening engine coolant additives. The working electrode of the quartz crystal 11 microbalance could be subjected to a flow of water/glycol mixture. The flow could be maintained constant and the crystal 11 held at a constant skin temperature. The amount of heat sufficient to freeze the fluid would be withdrawn through the surface of the crystal 11 using a Peltier element or a refrigeration rod. This would lead to the formation and growth of a frozen layer on the crystal 11, the mass of which would be measured in situ. The effect of adding anti-freeze chemicals to the bulk liquid could be evaluated similar to the evaluation illustrated graphically in FIG. 5.

The method and apparatus of the present invention could be used by way of a stationary device, on-line or portable device and can be used to measure thermal fouling in aqueous and non-aqueous solutions including, but not limited to, cooling water systems, pulp and paper processing, food and beverage, pharmaceutical, semiconductor, petrochemical and chemical processes. The method and apparatus of the present invention can be used to rate the fouling propensity of industrial liquids at specified thermal transfer rates and specified electrochemical conditions. The method and apparatus are applicable to the formation of any type of scale including, but not limited to: carbonate, sulfate and silicate scaling and biofilm formation from water streams; and ice and wax formation from industrial hydrocarbon streams. The method can be used for relative measurements even if the deposit has substantial viscoelastic properties. These properties can be taken into the account by calibration or network analysis while computing the overall mass increase. The method and apparatus can be used to rate the efficacy of anti-fouling treatments, either physical or chemical, at specified thermal transfer and electrochemical conditions. The operating temperatures of a quartz crystal resonator are only limited by its maximum temperature of piezoelectricity or the Curie point. The preferred embodiment can be used at low pressure differences across the sensor surface. For higher pressures, compensation to adjust the pressure at both sides of the sensor may be utilized.

The present invention offers a number of advantages over the currently-established prior art. Current practice of fouling assessment relies heavily on measurements of heat transfer efficiency as described in, e.g., Sommerscale & Knudsen, Fouling of Heat Transfer Equipment, page 57, "Apparatus and Techniques for Measurement of Fouling of Heat Transfer Surfaces". These measurements have a number of significant shortcomings that are overcome by the present invention.

For example, the sensitivity of methods relying on heat transfer measurements is limited by the dependence of heat transfer rates on the flow characteristics of fluid streams. In field applications it can be very difficult to either compensate for the effects of flow on fluid heat transfer resistance or to hold the flow constant. Compounding the problem is the fact that fluid heat transfer resistance is impacted by changes in the roughness of the surface. Since the actual deposition rate is derived by inference from changes in the heat transfer rate in these methods, these limitations introduce a great deal of uncertainty and lack of precision in data derived from these methods. In contrast, the method of the present invention produces a direct measurement of deposition mass which is not derived indirectly from heat transfer data. This results in a more robust and reliable measurement which is less impacted by the conditions of field measurements.

Also, as previously described, heat transfer and corrosion/ electrochemical processes have an impact on deposition rates. In order to produce relevant data, a test probe is required to simulate the environment produced by the targeted surfaces. Fouling measurement methods relying on heat transfer efficiency or surface temperature measurements are inherently limited to heat transfer surfaces. Furthermore, these methods do not allow systematic simulation of the conditions produced by corrosion or other electrochemical processes. In contrast, the method of the present invention allows systematic simulation of all of these important parameters to the extent dictated by the situation.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method for measuring a rate of scale formation on a surface caused by a flowing liquid and a heat flux through the surface, the method comprising:
   a) providing a piezoelectric microbalance comprising piezoelectric material having a first side facing the liquid and a second opposing side, the first side engaging a working electrode, the second side engaging a second electrode;
   b) exposing the working electrode of the piezoelectric microbalance to the flowing liquid, the liquid containing at least one fouling species;
   c) maintaining the liquid at a constant first temperature;
   d) maintaining the liquid in a controlled flow environment;
   e) establishing a constant heat flux through the working electrode resulting in the electrode having a variable second temperature; and
   f) measuring a rate of precipitation on the electrode.

2. The method of claim 1 wherein step (e) further comprises simultaneously applying an electrochemical polarization to the working electrode.

3. The method of claim 1 wherein the step of maintaining the liquid in a controlled flow environment is accomplished hydrodynamically using an arrangement selected from the group consisting of an impeller, a channel, a tunnel, and a wall-jet.

4. The method of claim 1 wherein the step of establishing a heat flux is accomplished with a Peltier element.

5. The method of claim 1 wherein the step of establishing a heat flux is accomplished with an apparatus selected from the group consisting of a cartridge heater and a cartridge cooler.

6. The method of claim 1 wherein the step of establishing a heat flux is accomplished by heat exchange.

7. The method of claim 1 further comprising the following steps:
   g) adding an anti-scale treatment chemical to the liquid;
   h) re-measuring a rate of precipitation using the piezoelectric material after the addition of the treatment chemical.

8. The method of claim 1 further comprising the following steps:
   g) modifying the flow rate established in step (d);
   h) repeating steps (e) and (f).

9. The method of claim 1 further comprising the following steps:
   g) modifying the fluid temperature established in step (c);
   h) repeating steps (e) and (f).

10. The method of claim 1 further comprising the following step:
    g) reversing the heat flux applied in step (e) to clean the surface of the piezoelectric material.

11. The method of claim 2 further comprising the following step:
    g) reversing the electrochemical polarization applied in step (e) to clean the first surface of the piezoelectric microbalance.

12. A method for measuring a rate of scale formation on a surface caused by flowing liquid and a heat flux through the surface, the method comprising:
    a) providing a piezoelectric microbalance comprising piezoelectric material having a first side facing the liquid and a second opposing side, the first side engaging a working electrode, the second side engaging a second electrode;
    b) exposing the working electrode of the piezoelectric microbalance to a flowing liquid, the liquid containing at least one fouling species;
    c) maintaining the liquid at a constant first temperature;
    d) maintaining the liquid in a controlled flow environment;
    e) applying a variable heat flux across the piezoelectric material to maintain the working electrode at a constant second temperature; and
    f) measuring a rate of precipitation on the surface of the piezoelectric material and working electrode.

13. The method of claim 12 wherein step (e) further comprises simultaneously applying an electrochemical polarization to the working electrode.

14. The method of claim 12 wherein the step of maintaining the liquid in a controlled flow environment is accomplished hydrodynamically using an arrangement selected from the group consisting of an impeller, a channel, a tunnel, and a wall-jet.

15. The method of claim 12 wherein the step of applying a heat flux is accomplished with a Peltier element.

16. The method of claim 12 wherein the step of applying a heat flux is accomplished with an apparatus selected from the group consisting of a cartridge heater and a cartridge cooler.

17. The method of claim 12 wherein the step of applying a heat flux is accomplished by heat exchange.

18. The method of claim 12 further comprising the following steps:
    g) adding an anti-scale treatment chemical to the liquid;
    h) re-measuring a rate of precipitation using the piezoelectric material and working electrode after the addition of the treatment chemical.

19. The method of claim 12 further comprising the following steps:
    g) modifying the flow rate established in step (d);
    h) repeating steps (e) and (f).

20. The method of claim 12 further comprising the following steps:
    g) modifying the fluid temperature established in step (c);
    h) repeating steps (e) and (f).

21. The method of claim 12 further comprising the following step:
    g) reversing the heat flux applied in step (e) to clean the surface of the microbalance.

22. The method of claim 13 further comprising the following step:
    g) reversing the electrochemical polarization applied in step (e) to clean the microbalance surface.

23. A method for measuring the effectiveness of an anti-fouling additive in preventing fouling at a solid-liquid interface disposed in a flowing liquid and subjected to a heat flux, the method comprising:
    a) providing a piezoelectric microbalance comprising a piezoelectric material having a first side facing the liquid and a second opposing side, the first side engaging a working electrode, the second side engaging a second electrode, the second side of the piezoelectric material engaging a heat conductive material connected to a heat flux generator;
    b) exposing the working electrode to the flowing liquid, the liquid containing at least one fouling forming species;
    c) maintaining the liquid at a constant first temperature;
    d) maintaining the liquid in a controlled flow environment;
    e) simultaneously applying a heat flux through the piezoelectric material and the working electrode to maintain the working electrode at a constant second temperature and applying an electrochemical polarization to the working electrode;
    f) measuring a rate of precipitation using the piezoelectric microbalance;
    g) adding the anti-fouling additive to the liquid;
    h) repeating step (f).

24. A method for measuring the effectiveness of an anti-fouling additive in preventing fouling at a solid-liquid interface disposed in a flowing liquid and subjected to heat transfer, the method comprising:
    a) providing a piezoelectric microbalance comprising a piezoelectric material having a first side facing the liquid and a second opposing side, the first side engaging a working electrode, the second side engaging a second electrode, the second side engaging a heat conductive material connected to a heat flux generator;
    b) exposing the working electrode to the flowing liquid, the liquid containing at least one fouling species;
    c) maintaining the liquid at a constant first temperature;
    d) maintaining the liquid in a controlled flow environment;

e) simultaneously applying a constant heat flux through the piezoelectric microbalance to maintain the working electrode thereof at a variable second temperature and applying an electrochemical polarization to the electrode;

f) measuring a rate of precipitation using the piezoelectric microbalance;

g) adding the anti-fouling additive to the liquid;

h) repeating step (f).

25. An apparatus for simulation of fouling on a liquid/equipment surface interface caused by a heat flux through the surface, the apparatus comprising:

a piezoelectric microbalance comprising a first surface for exposure to the liquid and a second surface located near heat conducting block, the first surface having a working electrode disposed thereon, the second surface and block being isolated from the liquid by a seal, the heat conducting block being connected to a heat flux generator.

26. The apparatus of claim 25 further comprising a hydrodynamic arrangement selected from the group consisting of an impeller, a channel, a tunnel, and a wall-jet for providing a controlled flow environment for the liquid coming in contact with the immersed surface of the piezoelectric microbalance.

27. The apparatus of claim 25 wherein the heat flux generator is a Peltier element.

28. The apparatus of claim 25 wherein the heat flux generator is selected from the group consisting of a cartridge heater and a cartridge cooler.

29. The apparatus of claim 25 wherein the heat flux is generated by heat exchange.

* * * * *